(12) United States Patent
Filho

(10) Patent No.: US 6,503,258 B1
(45) Date of Patent: Jan. 7, 2003

(54) UNITARY ANASTOMOTIC DEVICE

(76) Inventor: Luiz Gonzaga Granja Filho, Rua Muniz Tavares 147/801, 52050-170 Recife PE (BR)

( * ) Notice: Subject to any disclaimer, the term of this patent is extended or adjusted under 35 U.S.C. 154(b) by 0 days.

(21) Appl. No.: 09/528,930

(22) Filed: Mar. 20, 2000

(51) Int. Cl.$^7$ ............................................... A61B 17/04
(52) U.S. Cl. ..................................................... 606/153
(58) Field of Search ................................ 606/153–155

(56) References Cited

U.S. PATENT DOCUMENTS

| | | | | |
|---|---|---|---|---|
| 3,254,651 A | * | 6/1966 | Collito | 606/155 |
| 3,265,069 A | * | 8/1966 | Healey et al. | 606/153 |
| 3,774,615 A | * | 11/1973 | Lim et al. | 606/153 |
| 4,366,819 A | * | 1/1983 | Kaster | 606/153 |

* cited by examiner

*Primary Examiner*—Gary Jackson
(74) *Attorney, Agent, or Firm*—Michael I Kroll

(57) ABSTRACT

The present invention 10 discloses a prosthetic device used for end to side, end to end, and side to side anastomosis without clamping and suture or without suture but with clamping wherein the graft is inserted into the lumen 17 of the tubular member 18 of the prosthesis having a diameter approximately equal to the inside diameter of the tubular member 18 of the prosthesis for end to end and end to side anastomosis and can be everted 28 to cover that part of the prosthesis that will reside within the vein, artery or other tubular organ 12 and affixed to the base of the prosthesis by a circular suture 30. The tubular member 18 of the prosthesis 10 is attached to a base flange member 16 having apertures 24 therein which allow the flange 16 to be stitched to the outside of the aorta or other tubular organ 12 to eliminate the introduction of foreign bodies into the lumen of the anastomosis. The prosthesis 10 can be manufactured in varying sizes to accommodate varying sizes of grafts 14 and may have bezelled edges 38, a border 36 and be U-shaped 40 and it can also be cut in halves. The prothesis can be made of titanium, stainless steel, silicone, biodegradable materials, or of any other inert materials. The prothesis 10 makes it possible to do any kind of vascular, intestinal, urinary, choledochal anastomosis or anastomosis between any two tubular organs.

15 Claims, 14 Drawing Sheets

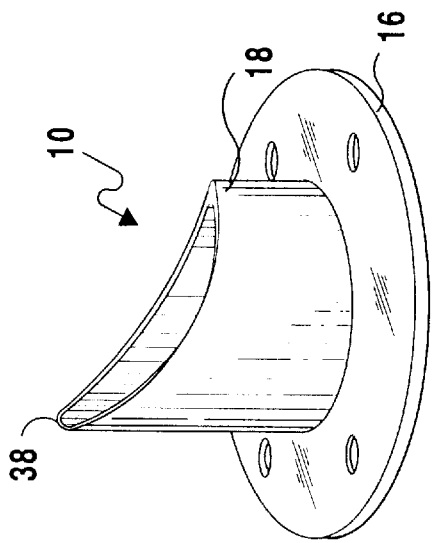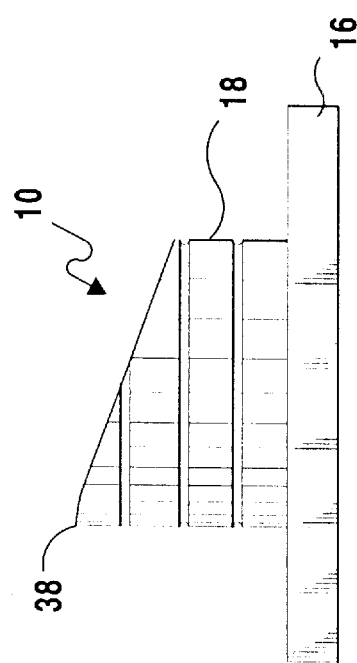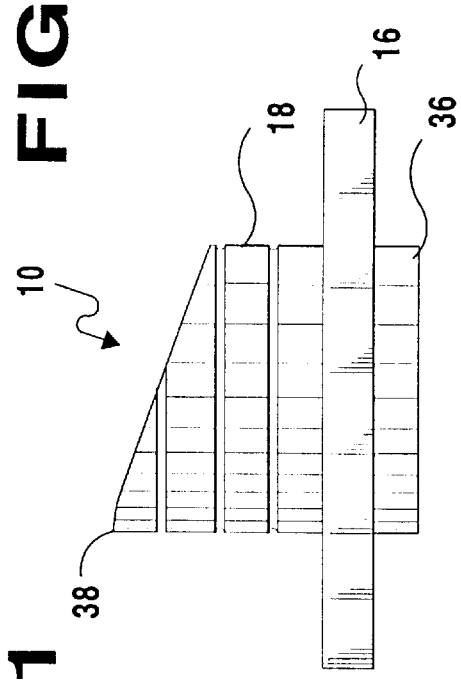
FIG 11A
FIG 11
FIG 11B

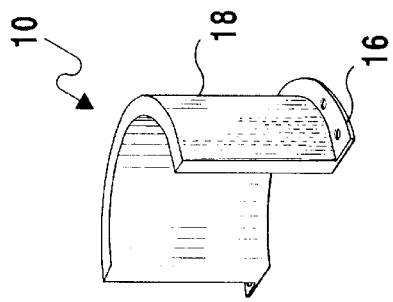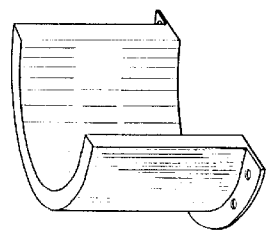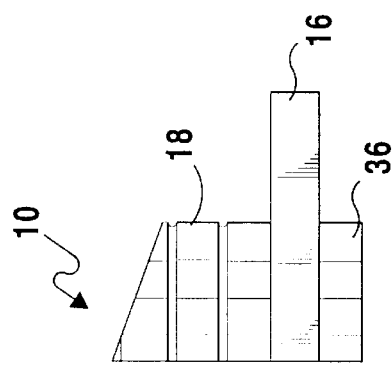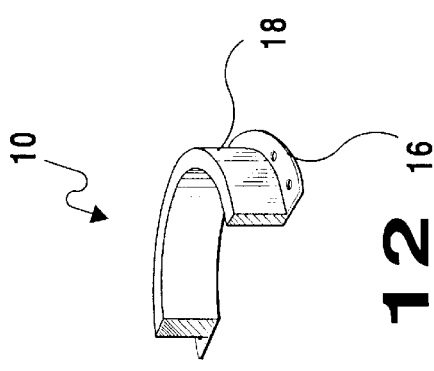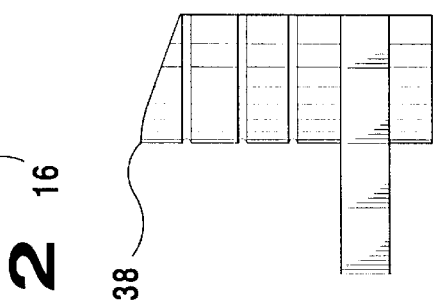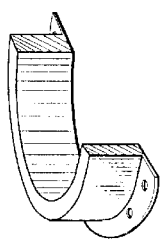
FIG 12A
FIG 12B
FIG 12

UNITARY ANASTOMOTIC DEVICE

BACKGROUND OF THE INVENTION

1. Field of the Invention

The present invention relates generally to anastomotic devices and, more specifically to a prosthetic device for end to side anastomosis without clamping and without suture whereby the vascular graft is inserted into the lumen of the prosthesis and having a diameter equal to the inside diameter of the prosthesis is everted to cover that part of the prosthesis that will reside within the vein or artery and is affixed to the base of the prosthesis by a circular stitch. The base of the prosthesis having a plurality of holes spaced on the periphery of the prosthesis allows the prosthesis to be sutured to said vein, artery or any other tubular organ outside of the anastomosis thereby eliminating one of the major causes of anastomosis obstruction which is the introduction of foreign bodies into the lumen of the anastomosis. This prosthesis further eliminates the need for clamping which diminishes the occurrence of arterial, cerebral and systemic trombo-embolic complications which when taken into consideration with the fact that the number of myocardial revascularization surgeries alone is rapidly approaching one million worldwide will result in substantial savings in human life not only from the aforementioned complications but the intangible value derived by the patients by not having to endure additional surgical procedures thereby allowing them to more quickly return to a more normal lifestyle as well as reducing the enormous expense associated with these additional surgical procedures which currently burden the health care system.

2. Description of the Prior Art

There are other anastomotic devices designed to correct vascular abnormalities. Typical of these is U.S. Pat. No. 3,254,650 issued to Collito on Jun. 7, 1966.

Another patent was issued to Healey, Jr., et al on Aug. 9, 1966 as U.S. Pat. No. 3,265,069. Yet another U.S. Pat. No. 3,774,615 was issued to Lim et al. on Nov. 27, 1973 and still yet another was issued on Jan. 4, 1983 to Kaster as U.S. Pat. No. 4,366,819.

While these anastomotic devices may be suitable for the purposes for which they were designed, they would not be as suitable for the purposes of the present invention, as hereinafter described.

SUMMARY OF THE PRESENT INVENTION

The present invention discloses a prosthetic device used for end to side anastomosis without clamping and without suture wherein the vascular graft vein is inserted into the lumen of the tubular member of the prosthesis having a diameter approximately equal to the inside diameter of the tubular member of the prosthesis and can be everted to cover that part of the prosthesis that will reside within the vein or artery and affixed to the base of the prothesis by a circular suture. The tubular member of the prosthesis is attached to a base flange member having apertures therein which allow the flange to be stitched to the outside of the aorta to eliminate the introduction of foreign bodies into the lumen of the anastomosis. The prosthesis can be manufactured in varying sizes to accomodate varying sizes of grafts. Also, the device may have bezelled edges, a border ,U-shaped, and be cut in halves.

A primary object of the present invention is to provide an end to side anastomotic device without clamping and suture.

Another object of the present invention is to provide an anastomotic device having a tubular member for inserting a graft.

Yet another object of the present invention is to provide anastomotic device having a plurality of circular ridges on the exterior of said tubular member as means for affixing the everted graft to said tubular member.

Still yet another object of the present invention is to provide an anastomotic device having a flange located on one distal end of said tubular member.

Yet another object of the present invention is to provide an anastomotic device having a plurality of holes located on the periphery of said flange as means for attaching said flange to the wall of the organ to be anastomized, may it be an artery, a vein or any other tubular organ.

Another object of the present invention is to provide an anastomotic device, which does not introduce any foreign bodies within the anastomosis graft.

Yet another object of the present invention is to provide an anastomotic device for manufacture in varying sizes so that the internal diameter of the prosthesis is compatible with the external diameter of the graft.

Still yet another object of the present invention is to provide an anastomotic device, which does not require clamping during the surgical procedure.

Additional objects of the present invention will appear as the description proceeds.

The present invention overcomes the shortcomings of the prior art devices by providing an anastomotic device that eliminates the introduction of foreign bodies into the lumen of the anastomosis. The invention further eliminates the need for clamping which diminishes the occurrence of arterial, cerebral and systemic trombo-embolic complications.

The foregoing and other objects and advantages will appear from the description to follow. In the description reference is made to the accompanying drawings, which form a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWINGS

In order that the invention may be more fully understood, it will now be described, by way of example, with reference to the accompanying drawings in which:

FIG. 11 is an elevation view of the present invention with a bezel led blunt edge.

FIG. 11A is a perspective view of the present invention with a bezelled blunt edge.

FIG. 11B is a perspective view of the present invention with a bezelled blunt edge and a border.

FIGS. 12–12A are perspective views of the present invention cut in half.

FIG. 12B is an elevation view of the present invention cut in half, with a border.

DESCRIPTION OF THE PREFERRED EMBODIMENT(S)

Figure 1:
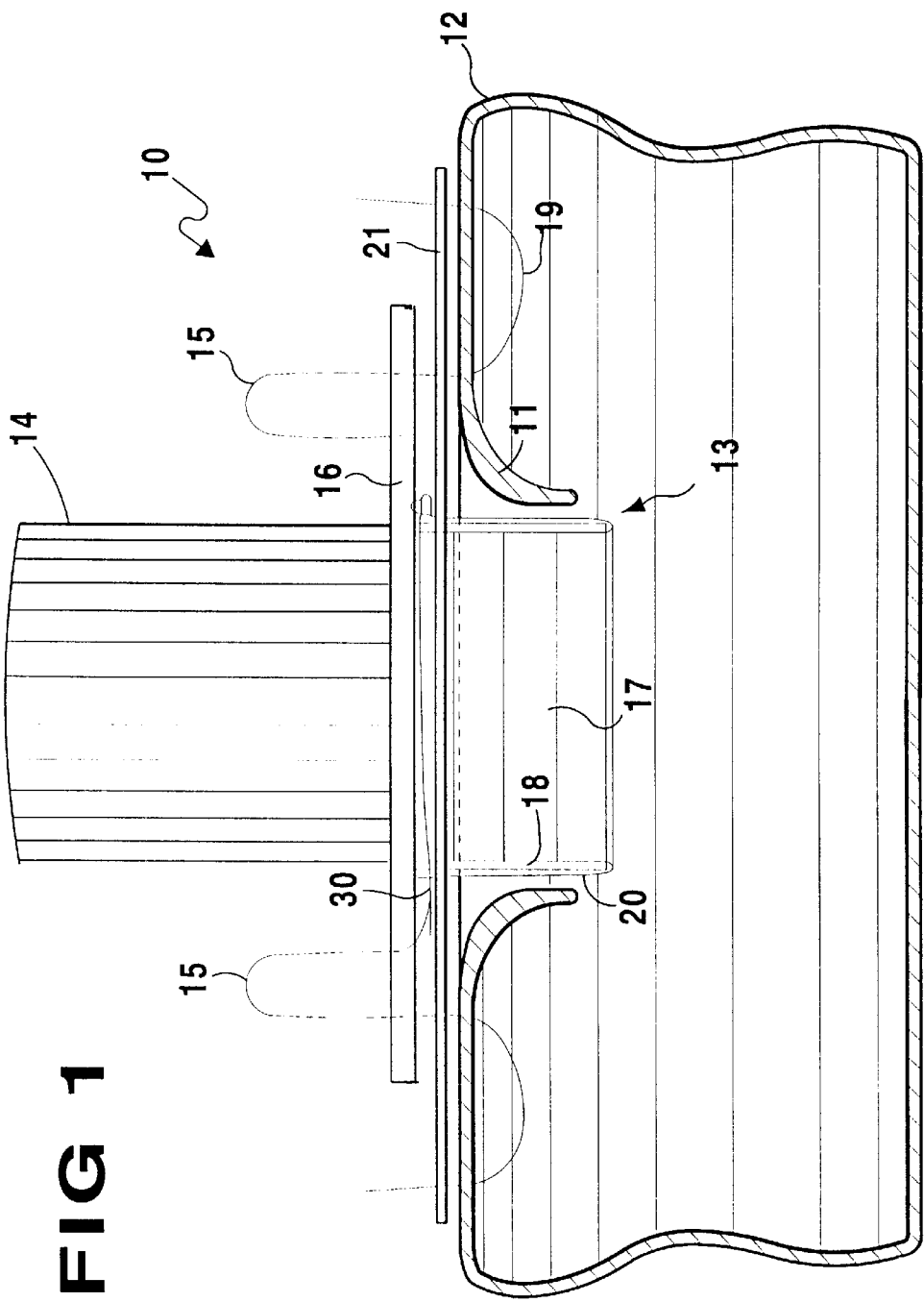
FIG. 1 is a sectional view of the present invention in use showing the invagination of the aorta wall into the anastomosis area determining the conical form of the intraluminal part of the prosthesis and graft.

Turning now descriptively to the drawings, in which similar reference characters denote similar elements throughout the several views, FIGS. 1 through 8 illustrate the present invention being a prosthesis for end to side anastomosis.

Turning to FIG. 1, therein is shown a sectional view of the present invention 10 in use showing the invagination 11 of the aorta wall 12 into the anastomosis area generally shown at 13 determining the conical form of the intraluminal part of the prosthesis and graft. Shown therein is the vein 14, which is to be grafted to and inserted into the side of aorta 12. The present invention 10 comprises a flange 16 and a tubular portion 18. The vein or first tubular body member 14 to be grafted to the aorta or second tubular body member 12 is passed through the interior of the lumen 17 of the tubular member 18 of the present invention 10 and everted at 20 around the end of said intraluminal end of the tubular member 18. The flange member 16 of the present invention 10 is then sewn by suturing 15 to the aorta 12 so as to promote a mating of the end of vein 14 into and with the side of aorta 12. Also shown is the suture line 15 passing through the flange 16 toward the intraluminal pathway 19 of the suture line 15. An additional suture 30 attaches the end of the everted vein 14 to the tubular wall 18. A section of reinforcement pericardium 21 is located between the flange 16 and aorta wall 12.

Figure 2:
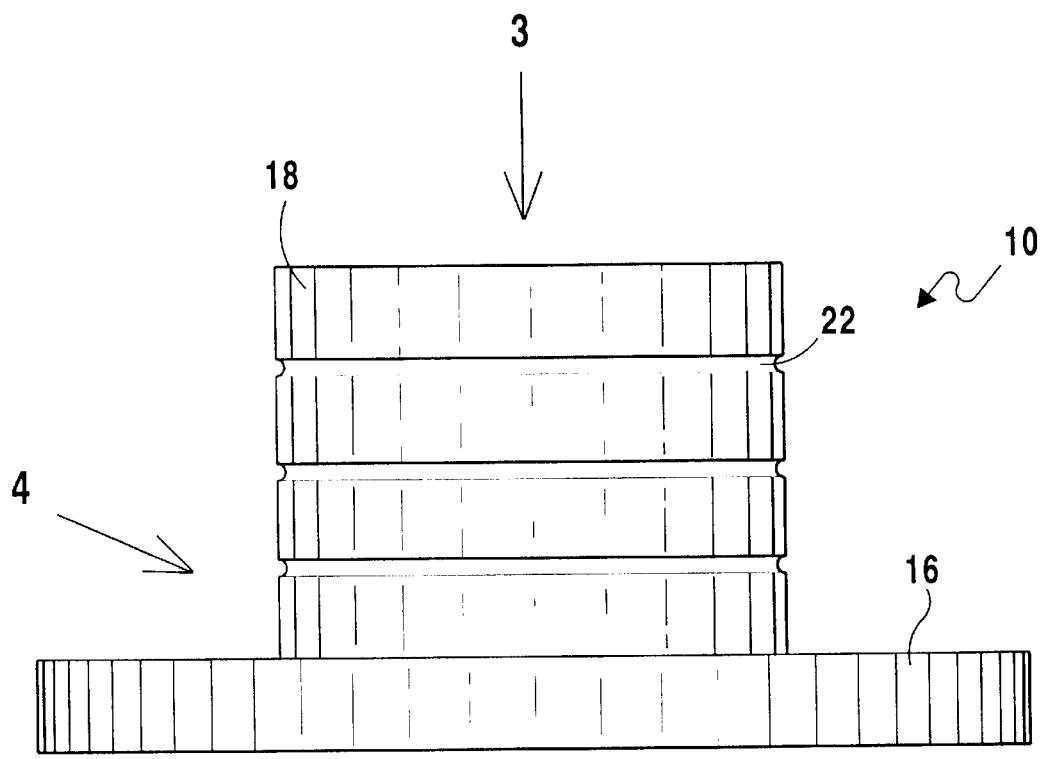
FIG. 2 is a front elevation of the present invention.

Turning to FIG. 2, therein is shown a front elevation view of the present invention 10. Shown therein is a tubular member 18, which is attached to a flange base member 16. It can be seen that the tubular member 18 has a plurality of grooves 22 located on its exterior wall providing means for securing the end of an everted vein thereto.

Figure 2A:
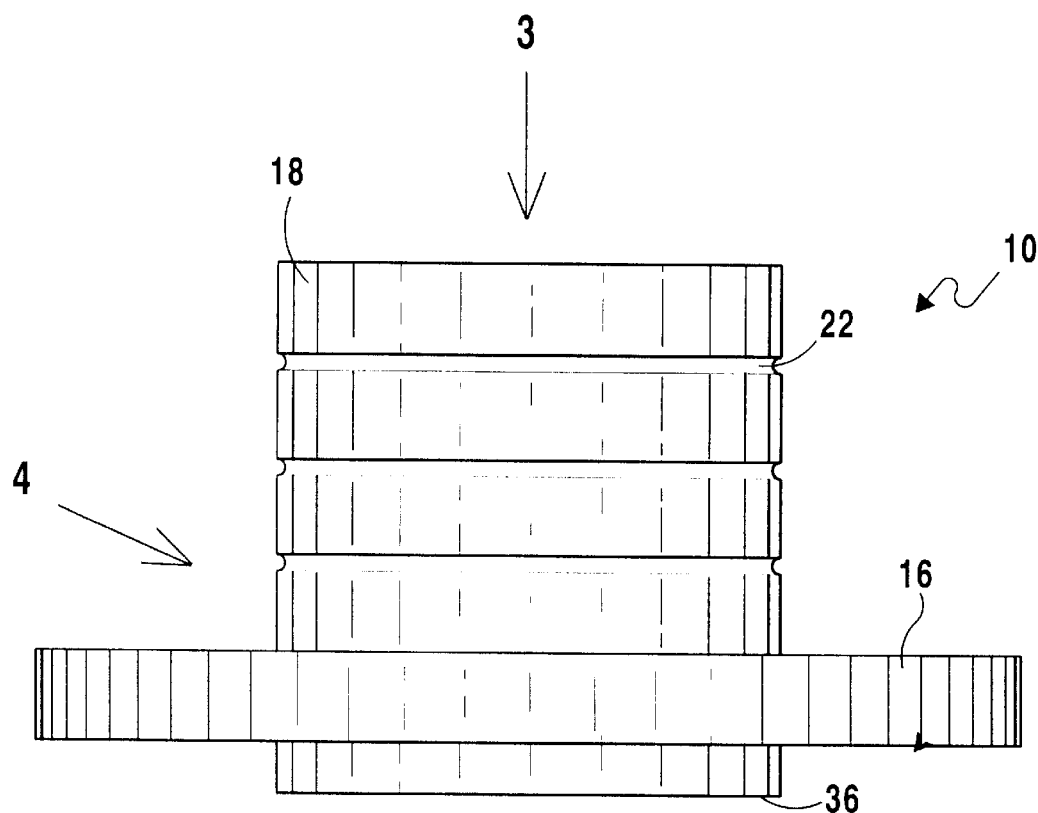
FIG. 2A is a front elevation of the present invention showing a border.

Turning to FIG. 2A, therein is shown a front elevation view of the present invention including the elements as disclosed in FIG. 2 and also showing a border 36. A border is generally necessary in all prosthesis of large caliber, i.e., larger than about 5 mm, and has the purpose to fix the legs of the suture lines in an arched form about the external peripheral edge of the border 36 so as to prevent the suture lines from invading the internal diameter of the prosthesis 10.

Figure 3:
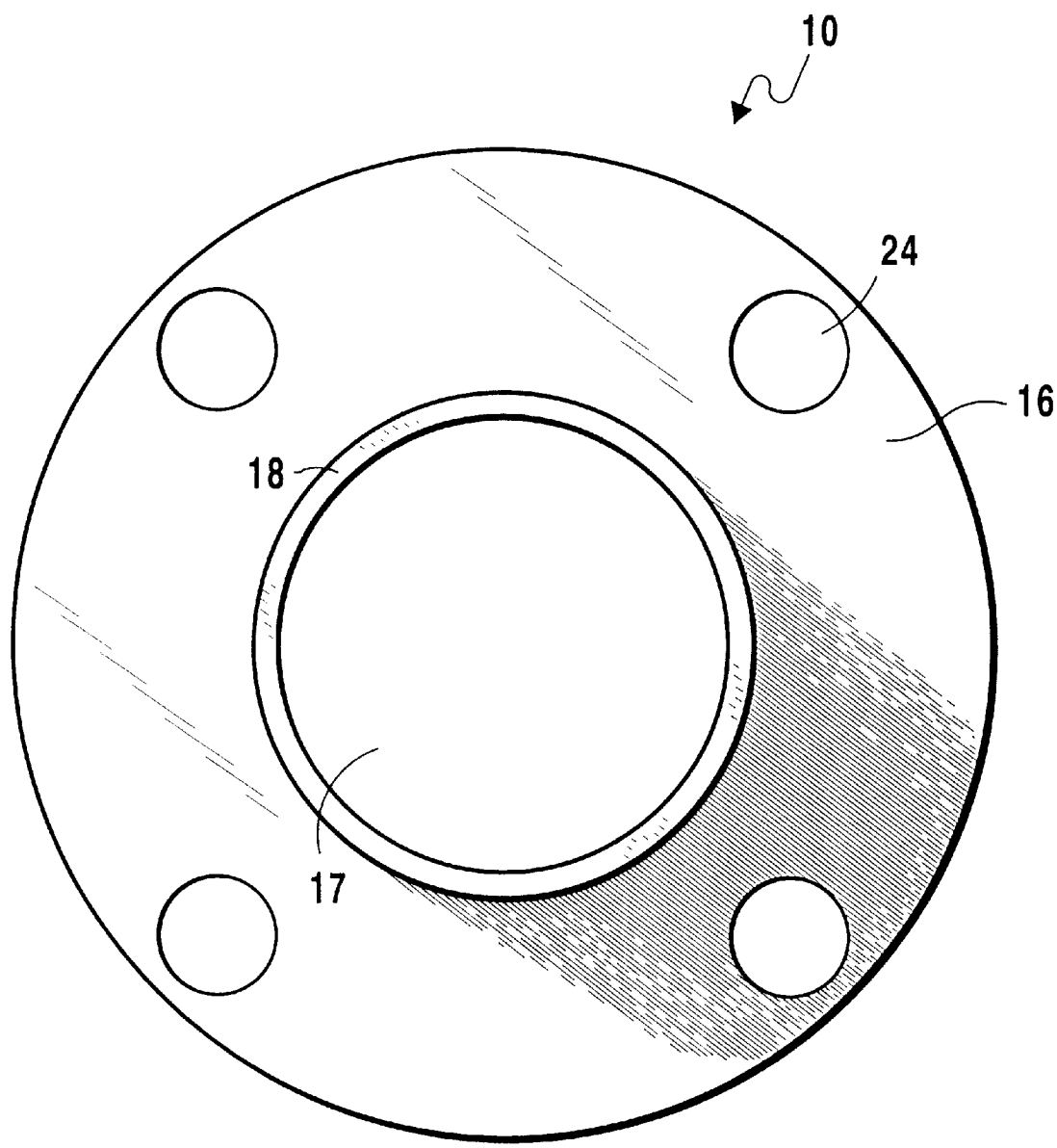
FIG. 3 is a top plan view of the present invention showing a plurality of openings in the flange portion of the prosthesis which are used as means for securing the prosthesis by suturing to a vein, artery, or any other tubular organ.

Turning to FIG. 3, therein is shown a top plan view of the present invention 10 showing a plurality of apertures or openings 24 through a flange portion 16 of the prosthesis which is used as means for securing the prosthesis to a vein or artery (not shown) by providing a pathway for sutures (not shown) to pass. Also shown is the tubular wall 18 having its opening or lumen 17 therein.

Figure 4:
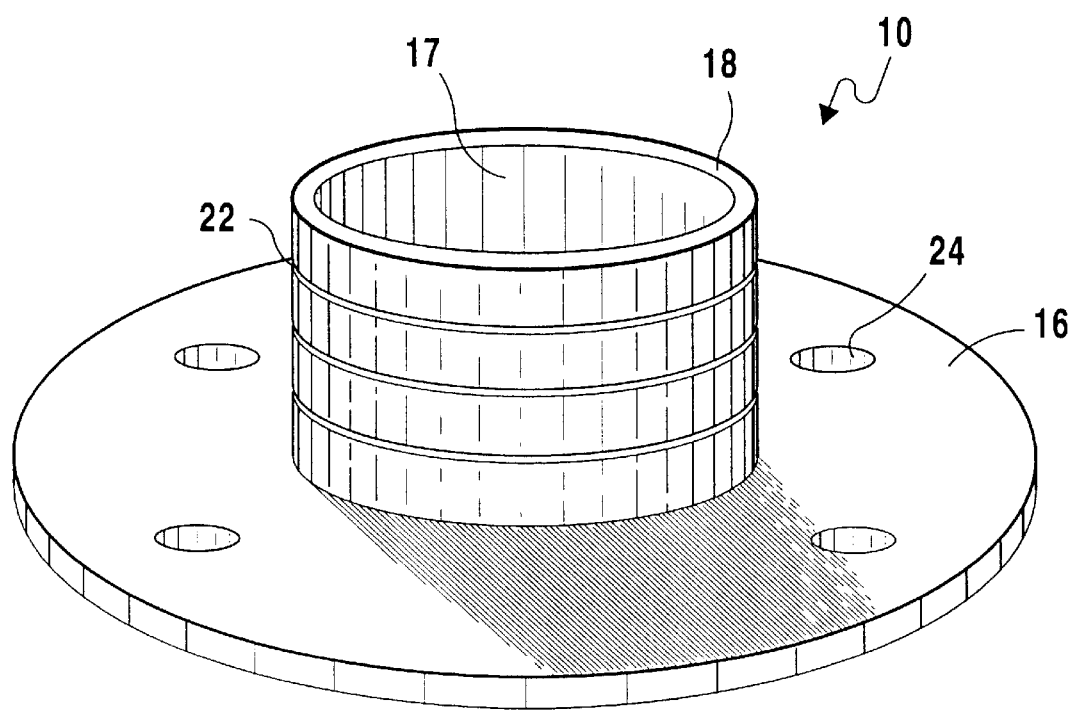
FIG. 4 is a perspective view of the present invention. Shown is a smooth bore tubular member having a plurality of grooves located within the exterior wall providing means for securing the graft after eversion of the graft. Also shown are a plurality of apertures located on the periphery of the flange portion of the prosthesis providing means for securing said prosthesis to a vein, artery or any other tubular organ outside of the anastomosis.

Turning to FIG. 4, therein is shown a perspective view of the present invention 10 showing a smooth bore tubular member 18 having a plurality of grooves 22 located within its exterior wall providing means for securing the graft after eversion of the graft. Also shown are a plurality of apertures 24 located on the periphery of the flange 16 portion of the prosthesis. Also shown is the tubular opening 17.

Figure 5:
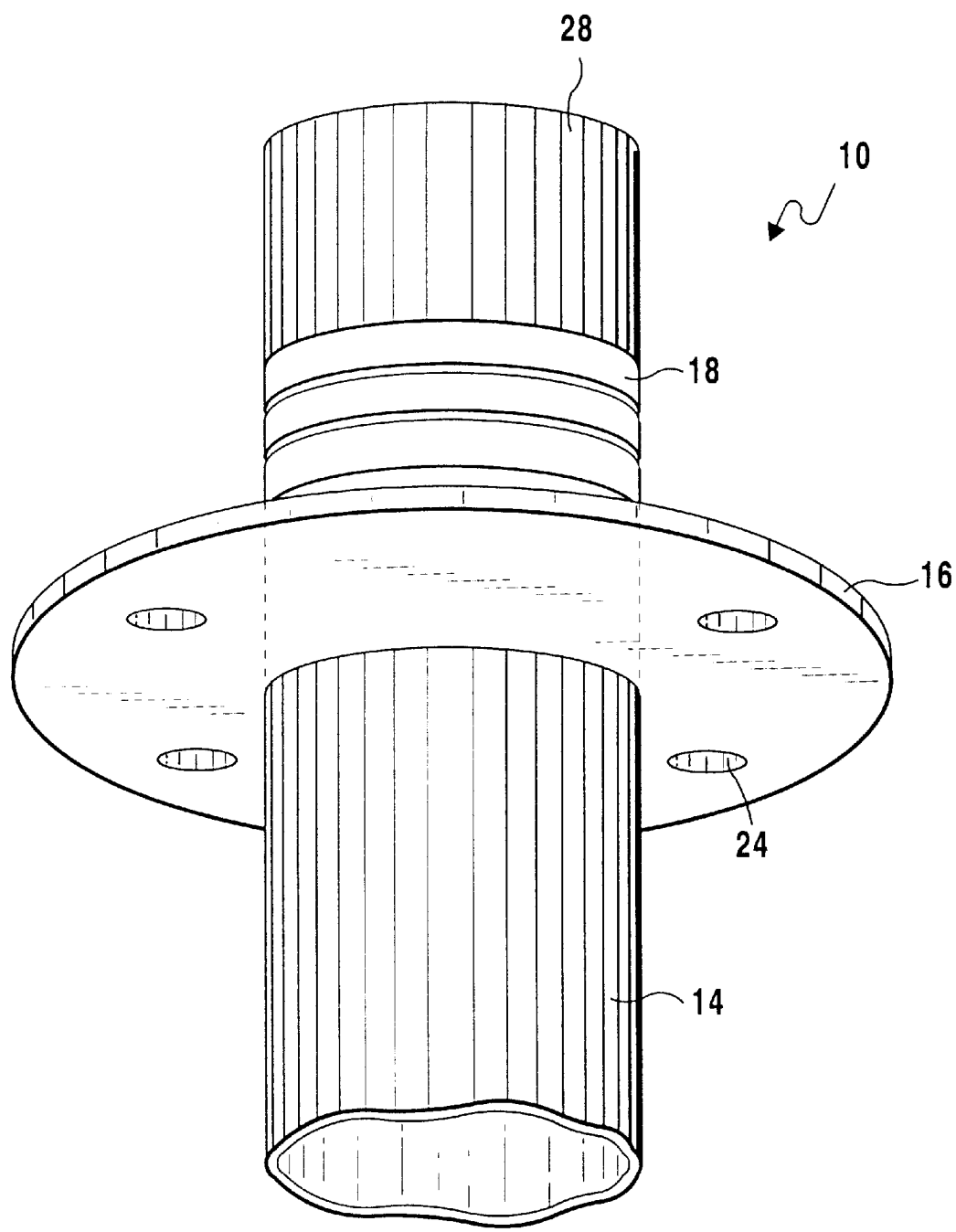
FIG. 5 is a front perspective view of the present invention showing the graft, which has been inserted into the prosthesis from the flange end of the bore and has been positioned for eversion of the graft.

Turning to FIG. 5, therein is shown a front perspective view of the present invention 10 showing the graft vein 14 which has been inserted into the prosthesis 10 from the flange 16 end of the bore or lumen and has been positioned for eversion of the graft at 28; this part of the vein 14 will then be everted over the tubular wall 18. Also shown are the apertures of the flange 24.

Figure 6:
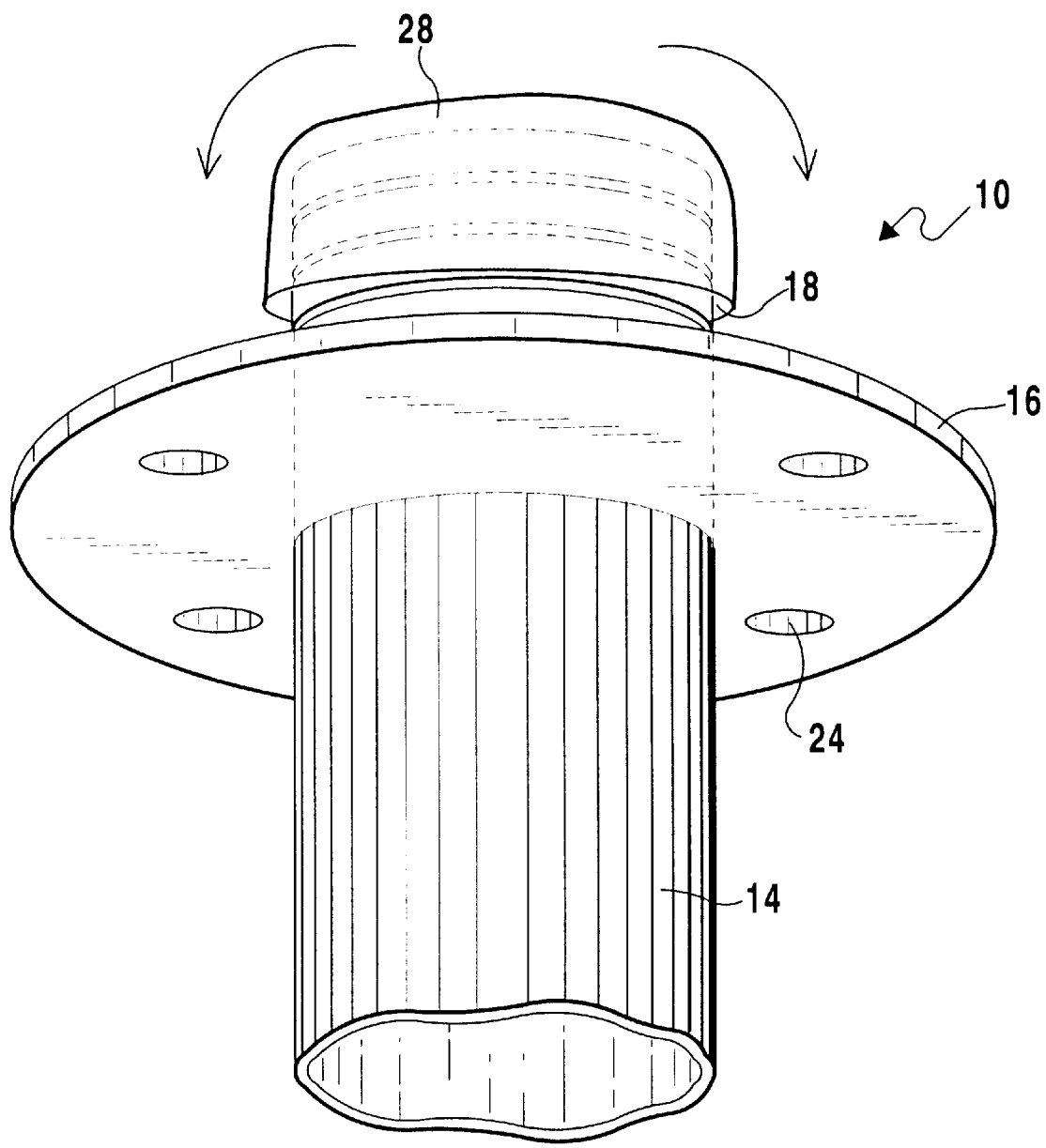
FIG. 6 is a front perspective view of the present invention showing the graft being everted over the tubular member of the prosthesis.

Turning to FIG. 6, therein is shown a front perspective view of the present invention 10 showing the end of the graft being everted at 28 over the tubular member 18 of the prosthesis 10. Also shown therein is the vein 14 or graft along with the flange 16 and the apertures 24 of the flange 16.

Figure 7:
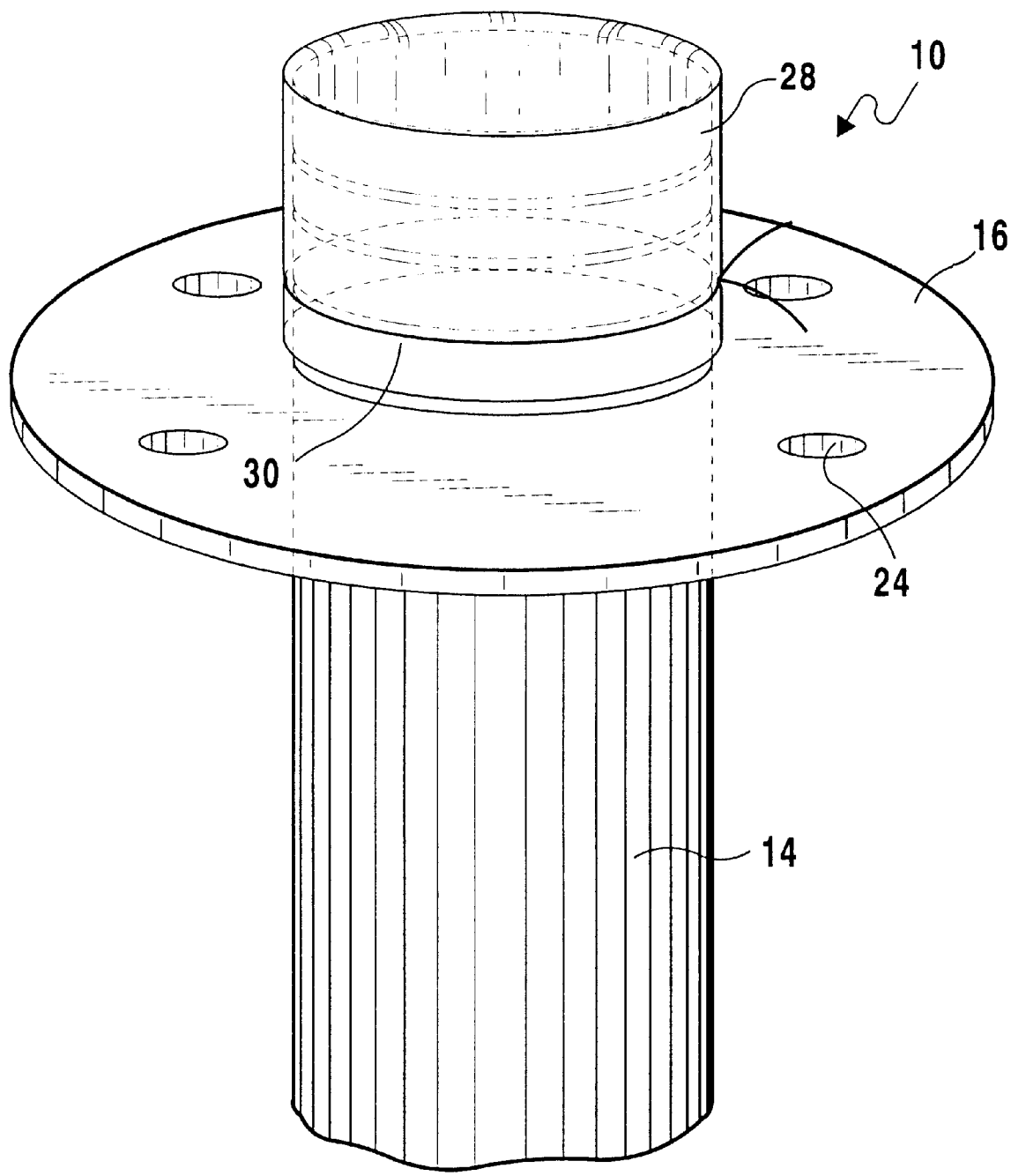
FIG. 7 is a perspective view of the present invention showing the graft completely everted over the tubular member of the prosthesis and being held to said prosthesis by means of a circular stitch which will maintain the position of the graft.

Turning to FIG. 7, therein is shown a perspective view of the present invention 10 showing the graft 28 completely everted over the end of the tubular member 18 of the prosthesis 10 and being held to said prosthesis by means of a circular stitch or suture 30 which will maintain the position of the graft 28. Also shown is the graft 14 along with the flange 16 and the apertures of the flange 24.

Figure 8:
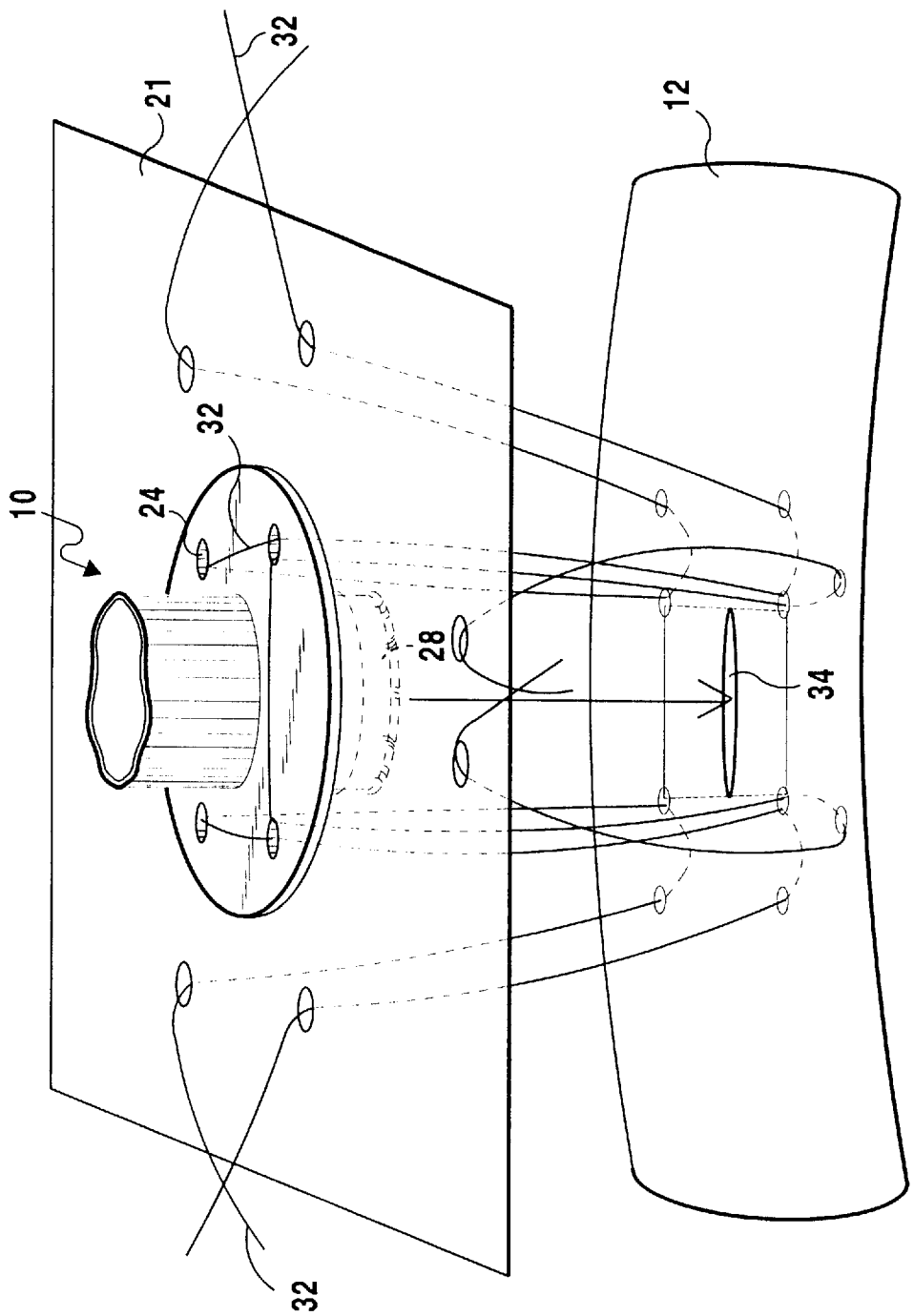
FIG. 8 is a perspective view of the present invention showing the graft ready to be inserted into a vein or artery. Also shown are the pathways followed by the suture lines. Considering that one suture line has one needle at each end, one of these ends passes through one of the peripheral holes of the prothesis then through the pericardium, then through the vein, artery or any other tubular organ and the back through the peripheral pericardium (or any other synthetic graft) and the other end of the suture line follows the same procedure through the adjacent peripheral hole of the prothesis. Three other stitches will be done following the same procedure.
Figure 9C:
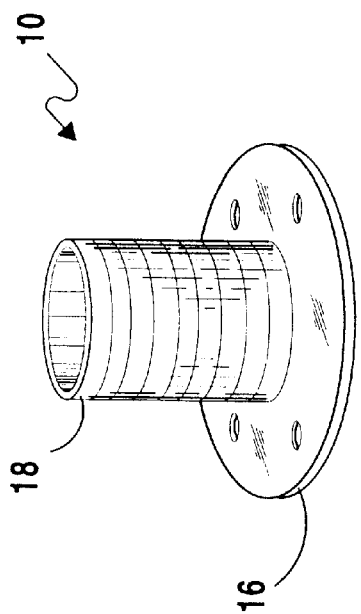
FIGS. 9–9D are perspective views of the present invention showing intraluminal parts of varying length.
Figure 9D:
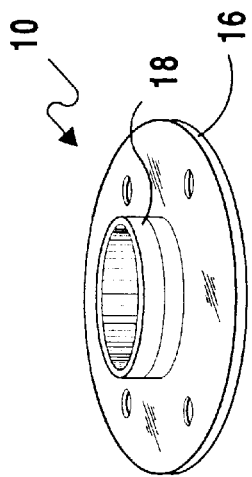
Figure 9:
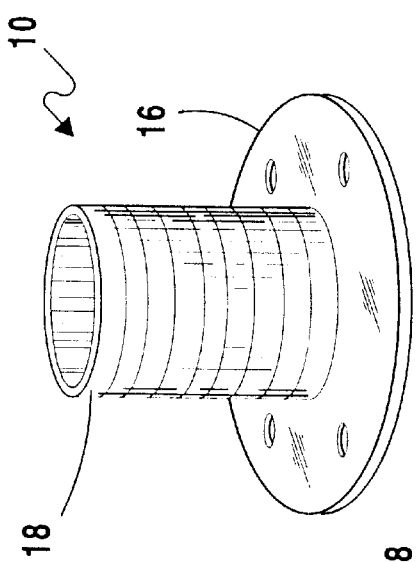
Figure 9B:
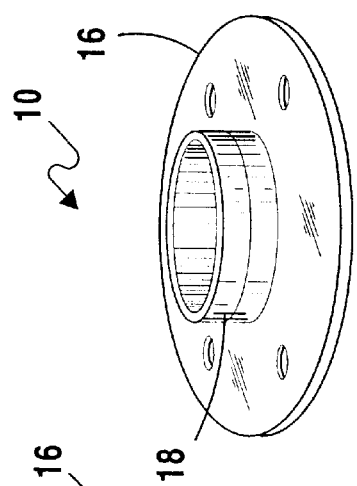
Figure 9A:
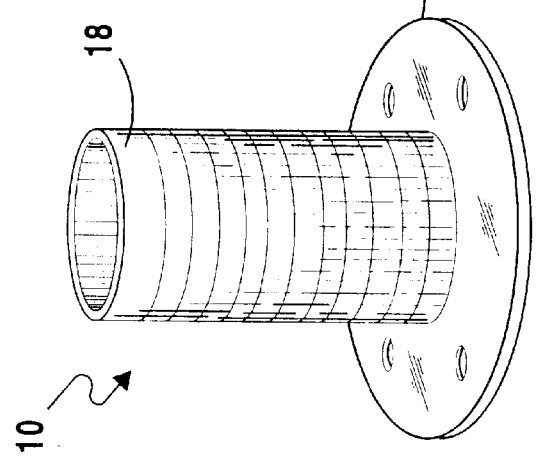

Turning to FIG. 8, therein is shown a perspective view of the present invention 10 showing the intraluminal part of the graft 28 ready to be inserted into aorta 12 by insertion through the aorta incision 34. Also shown are the fixation suture lines 32 passing through the flange holes 24, the reinforcement pericardium 21, into and out of the vein or artery 12, and back through the holes toward the periphery of the pericardium 21. Turning to FIGS. 9–9D, therein are shown perspective views of the present invention showing intraluminal walls 18 of varying lengths. The longer intraluminal parts 18 shown in FIGS. 9, 9C and 9D are for the purpose of colostomy, ileostomy, etc. while the short intraluminal part 18 of FIG. 9B is for anastomosis, esophageal, etc. Other elements previously disclosed are also shown.

Figure 10C:
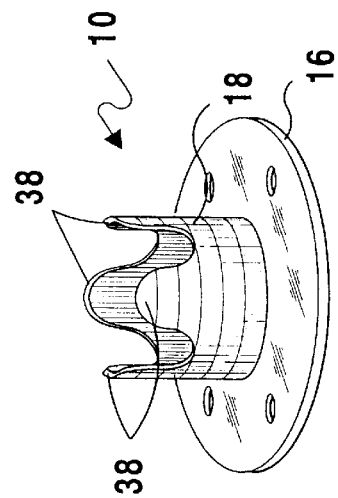
FIGS. 10–10C are perspective views of the present invention showing various designs of bezeled blunt edges. The importance of the blunt edge is to avoid the risk of cutting the inverted graft with a sharp or pointed end.
Figure 10A:
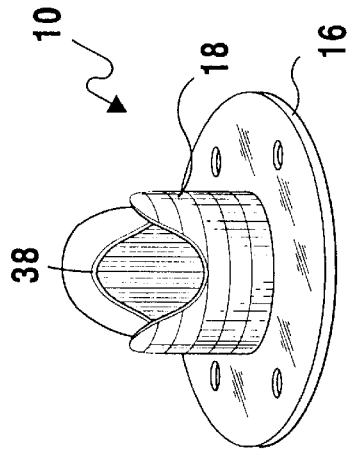
Figure 10B:
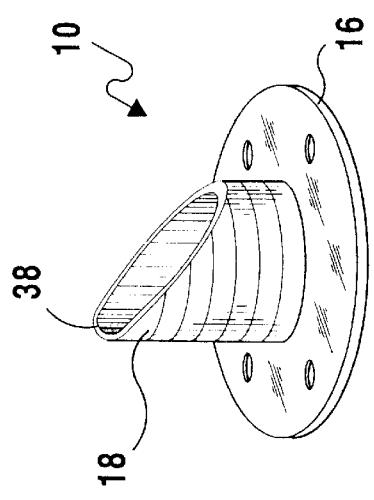
Figure 10:
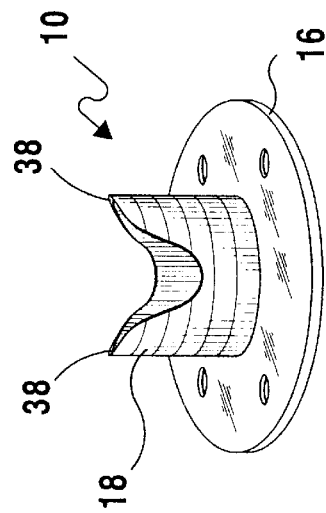

Turning to FIGS. 10–10C, therein are shown the present invention 10 with various designs of bezelled edges 38 relative to the tubular wall 18. The number of bezelled edges can vary from one as shown in FIG. 10B to four, or more, as shown in FIG. 10C Other elements previously disclosed are also shown.

Turning to FIG. 11, therein is shown an elevation view of the present invention 10 with a bezelled edge 38. Other features previously disclosed are also shown.

Turning to FIG. 11A, therein is shown a perspective view of the present invention 10 with a bezelled edge 38. Other features previously disclosed are also shown.

Turning to FIG. 11B, therein is shown an elevation view of the present invention 10 with a bezelled edge 38 and border 36. Other features previously disclosed are also shown.

Turning to FIGS. 12–12A, therein are shown perspective views of the present invention 10 cut in half showing features previously disclosed. The advantages are due to the bezelled edge are that it enlarges the anastomosis area; and it can be catheterized more easily because the inferior part of the bezelled edge is at the level of the internal surface of the organ which has received the prosthesis. This might be necessary for radiographic re-study and/or balloon dilation of the anastomotic area. Further, it will not offer any resistance to an eventual dilation of the anastomosis if stenosis happens after the absorption of the suture lines because it is set up and anastomized with absorbable suture lines. Further, it has a border in large caliber prosthesis with the purpose of the border being to keep the external part of the prosthesis with the same width (about 2 mm) and with four holes to support the leg of the suture line.

Turning to FIG. 12B, therein is shown an elevation view of the present invention 10 cut in half showing elements previously disclosed.

Figure 13:
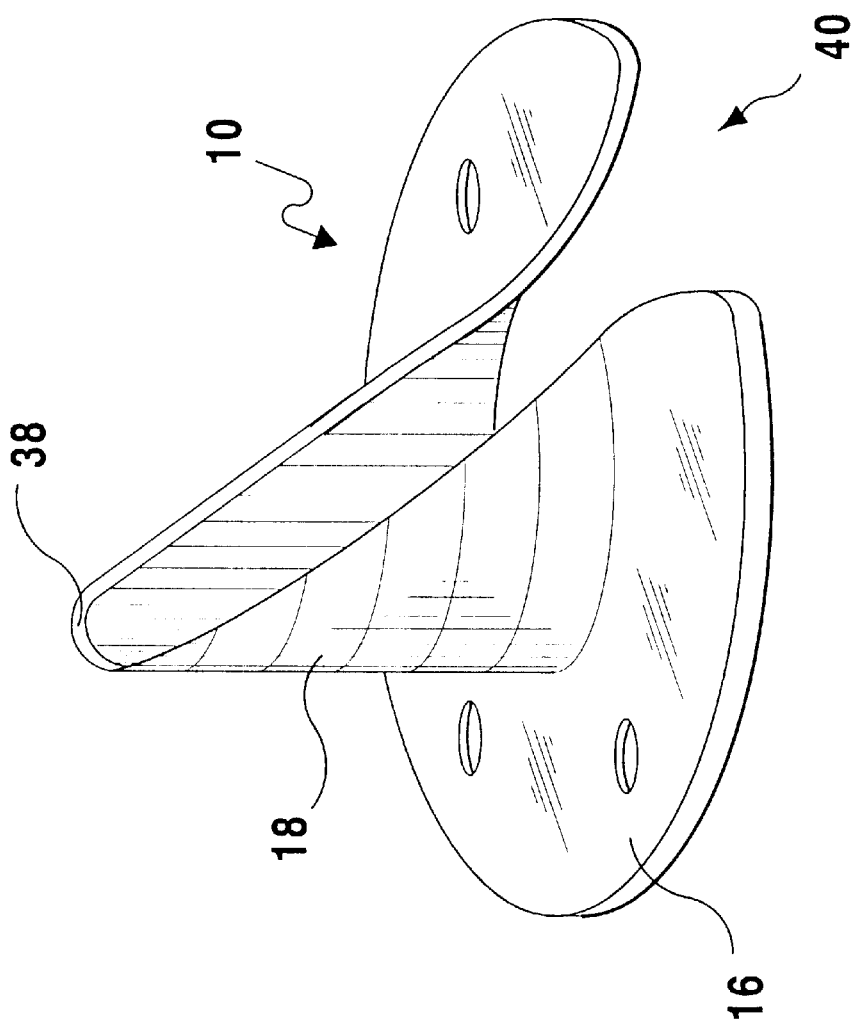
FIG. 13 is a perspective view of the present invention in a horseshoe form, which can also be U-shaped.

Turning to FIG. 13, therein is shown a perspective view of the present invention 10 in a horseshoe form 40, i.e., U-shaped, and bezelled edges 38. Its features are that it has a larger anastomosis area; it allows for the growth of the anastomosis area in growing organs, e.g., anastomosis done in children; and, it allows for anastomosis dilation with balloon. Other elements previously disclosed are also shown.

With reference to FIGS. 1–13, the method for this anastomosis technique comprises the following steps: (a) passing a vein 14 through the lumen of a tubular member 18 with the vein having the approximate same diameter as the tubular member and providing the tubular member 18 with a base flange 16 having a plurality of apertures 24 therein; (b) everting the end of the vein 14 around the outside end of the tubular member 18; (c) suturing the end of the vein 14 around the outside of the tubular member 18 with a circular suture 30 near the base flange 16; (d) making an incision 34 in the side wall of a tubular body member 12 for placement therein of the everted end 28 of the vein 14; (e) placing a piece of reinforcement pericardium 21 having a hole therein between the tubular member 18 and the tubular body member 12; (f) placing the everted end of the vein 28 inside the wall of the tubular body member 12; and, (g) suturing together the tubular member 18, the reinforcement pericardium 21, and the tubular body member 12 whereby anastomosis occurs. This procedure allows the prosthesis 10 to be sutured to said vein or artery or any other tubular organ 12 outside of the anastomosis area thereby eliminating one of the major causes of anastomosis obstruction, which is the introduction of foreign bodies into the lumen of the anastomosis. This prosthesis further eliminates the need for clamping which diminishes the occurrence of arterial, cerebral and systemic trombo-embolic complications.

What is claimed is:

1. A surgical device for anastomosis, comprising:
   (a) a tubular member;
   (b) said tubular member having a base flange attached in a generally perpendicular plane thereto; and,
   (c) said flange having a plurality of apertures therein adapted to be sutured to the end or the side of any tubular organ outside the anastomosis wherein said device allows a graft vein to be inserted and held within the tubular organ unsutured and wherein said tubular member varies in diameter to accommodate varying diameter of grafts.

2. The device of claim 1, said tubular member further comprising multiple grooves on its outer surface for attachement of an everted arterial, venous, or synthetic graft.

3. The device of claim 1, wherein said tubular member varies in length.

4. The device of claim 1, further comprising a border formed by said tubular member extending beyond the perpendicular plane of said flange.

5. The device of claim 1, wherein said tubular member has at least one bezelled edge.

6. The device of claim 1, wherein said device is U-shaped.

7. The device of claim 1, further comprising said device having two halves, said halves thereafter being joined together to form said tubular member.

8. The device of claim 1, wherein said tubular member has two halves, said halves being joined together to form a tubular member.

9. The device of claim 1 in which said base flange is between and spaced from ends of said tubular member.

10. The device of claim 1 in which said tubular member is adapted for insertion into said tubular organ and the length of said tubular member is selected to terminate within said tubular organ.

11. A method for anastomosis, comprising the steps of:
   (a) passing an end of a graft through a tubular member said graft having the approximate same diameter as the tubular member, providing said tubular member with a base flange having a plurality of apertures therein;
   (b) everting the end of said graft around the outside end of said tubular member;

(c) suturing the end of said graft around the outside of said tubular member with a circular suture near said base flange;
(d) making an incision in the side wall of a tubular body member for placement therein of said everted end of said graft;
(e) placing a piece of reinforcement graft having a hole therein between said tubular member and said tubular body member;
(f) placing said everted end of said graft inside the wall of said tubular body member; and,
(g) suturing together said tubular member, said reinforcement graft, and said tubular body member whereby anastomosis occurs.

12. The method of claim 11, further comprising the step of using a tubular member provided with multiple grooves on the outside for attaching said averted graft.

13. The method of claim 11, further comprising the step of preventing the introduction of foreign bodies into the lumen of the anastomosis.

14. The method of claim 12, further comprising the step of preventing the introduction of foreign bodies into the lumen of the anastomosis.

15. The method of claim 11, comprising the step of providing tubular members of varying sizes to accommodate grafts of varying sizes.

\* \* \* \* \*